(12) United States Patent
Zhan et al.

(10) Patent No.: US 9,851,290 B2
(45) Date of Patent: Dec. 26, 2017

(54) PARTICLE DETECTOR FOR PARTICULATE MATTER ACCUMULATED ON A SURFACE

(71) Applicant: Sharp Laboratories of America, Inc., Camas, WA (US)

(72) Inventors: Changqing Zhan, Vancouver, WA (US); Paul John Schuele, Washougal, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 0 days.

(21) Appl. No.: 14/746,739

(22) Filed: Jun. 22, 2015

(65) Prior Publication Data

US 2016/0370282 A1    Dec. 22, 2016

(51) Int. Cl.
*G01N 15/14*       (2006.01)
*G01N 21/59*       (2006.01)
*G01N 15/06*       (2006.01)
*G01N 15/00*       (2006.01)

(52) U.S. Cl.
CPC ..... *G01N 15/1434* (2013.01); *G01N 15/0606* (2013.01); *G01N 21/59* (2013.01); *G01N 2015/0046* (2013.01); *G01N 2015/1486* (2013.01); *G01N 2015/1493* (2013.01)

(58) Field of Classification Search
CPC ....... G01N 22/54373; G01N 33/54326; G01N 15/0656; G01N 33/5434; G01N 33/585
USPC ....... 356/246, 432, 39, 128, 300; 250/459.1, 250/458.1; 385/12, 14, 31, 37, 29, 129
See application file for complete search history.

(56) References Cited

U.S. PATENT DOCUMENTS

| | | | |
|---|---|---|---|
| 4,940,328 A * | 7/1990 | Hartman | ................. G01L 1/242 356/481 |
| 5,082,629 A | 1/1992 | Burgess, Jr. et al. | |
| 5,120,131 A * | 6/1992 | Lukosz | ............. G01N 21/7703 356/481 |

(Continued)

FOREIGN PATENT DOCUMENTS

| | | |
|---|---|---|
| JP | 2006029883 A | 2/2006 |
| WO | 8909394 A1 | 10/1989 |

(Continued)

OTHER PUBLICATIONS

Skrdla, P. et al., "Sol-Gel-Based, Planar Waveguide Sensor for Water Vapor," Analytical Chemistry, vol. 71, No. 7, Apr. 1999, 6 pages.

(Continued)

*Primary Examiner* — Sang Nguyen
(74) *Attorney, Agent, or Firm* — Steve Reiss; ScienBiziP, P.C.

(57) ABSTRACT

Particle detectors and methods for detecting particulate matter accumulated on a surface are provided. According to one aspect, the particle detector may comprise a substrate, an optical light source configured to emit light along a light path, a waveguide associated with the substrate, having a surface exposed to a gaseous environment and configured to accumulate on the surface particulate matter from the gaseous environment, a detector configured to receive the emitted light from the waveguide, and a controller configured to determine the intensity of the detected light and output an indication of an opacity of the surface of the waveguide with the accumulated particulate matter.

20 Claims, 7 Drawing Sheets

(56) References Cited

U.S. PATENT DOCUMENTS

| | | | |
|---|---|---|---|
| 5,125,740 A * | 6/1992 | Sato | G01N 21/43 356/128 |
| 5,192,502 A * | 3/1993 | Attridge | B01L 3/5027 356/246 |
| 5,405,583 A * | 4/1995 | Goswami | G01N 21/783 422/82.05 |
| 5,771,321 A * | 6/1998 | Stern | G02B 6/35 385/146 |
| 5,814,565 A * | 9/1998 | Reichert | G01N 33/54373 385/12 |
| 6,268,125 B1 | 7/2001 | Perkins | |
| 6,275,628 B1 * | 8/2001 | Jones | G02B 6/02057 385/29 |
| 6,316,274 B1 | 11/2001 | Herron et al. | |
| 6,499,355 B1 * | 12/2002 | Potyrailo | G01B 11/20 73/150 A |
| 6,903,815 B2 * | 6/2005 | Uchiyama | A61B 5/14525 356/300 |
| 7,444,053 B2 * | 10/2008 | Schmidt | G01N 21/0303 385/129 |
| 8,837,871 B2 | 9/2014 | Fujii et al. | |
| 8,857,242 B2 | 10/2014 | Heidrich et al. | |
| 2003/0032286 A1 * | 2/2003 | Deliwala | G02F 1/025 438/689 |
| 2004/0223151 A1 * | 11/2004 | Petros | G01N 21/7703 356/317 |
| 2005/0141843 A1 | 6/2005 | Warden et al. | |
| 2007/0146701 A1 * | 6/2007 | Kiesel | G01N 21/03 356/317 |
| 2007/0159628 A1 * | 7/2007 | Schmidt | B01J 8/228 356/336 |
| 2008/0180673 A1 * | 7/2008 | Sampas | G01N 21/648 356/432 |
| 2009/0069199 A1 * | 3/2009 | Brandenburg | G01N 21/6452 506/39 |
| 2009/0097031 A1 * | 4/2009 | Armani | G01N 21/7746 356/437 |
| 2009/0124024 A1 * | 5/2009 | Kasai | G01N 21/552 436/518 |
| 2009/0321661 A1 * | 12/2009 | Ohtsuka | G01N 21/05 250/459.1 |
| 2011/0236266 A1 * | 9/2011 | Uematsu | G01N 21/7703 422/82.11 |
| 2012/0214707 A1 * | 8/2012 | Ymeti | G01N 21/45 506/9 |
| 2012/0239797 A1 * | 9/2012 | Agrawal | H04L 41/12 709/224 |
| 2012/0252111 A1 | 10/2012 | Tono et al. | |
| 2012/0293797 A1 * | 11/2012 | Braeckmans | G01N 21/6458 356/246 |
| 2014/0319378 A1 * | 10/2014 | Van Steenberge | G01N 21/6428 250/459.1 |

FOREIGN PATENT DOCUMENTS

| | | |
|---|---|---|
| WO | 9635940 A1 | 11/1996 |
| WO | 2014116758 A1 | 7/2014 |

OTHER PUBLICATIONS

Lavers, C. et al., "Planar Optical Waveguides for Sensing Applications," Sensors and Actuators B: Chemical, vol. 69, No. 1-2, Sep. 2000, 11 pages.

Ksendzov, A. et al., "Integrated Optics Ring-Resonator Chemical Sensor with Polymer Transduction Layer," Electronics Letters, vol. 40, No. 1, Jan. 2004, 2 pages.

Liu, L. et al., "Absolute Position Total Internal Reflection Microscopy with an Optical Tweezer," Proceedings of the National Academy of Sciences of the United States of America, vol. 111, No. 52, Dec. 2014, 10 pages.

* cited by examiner

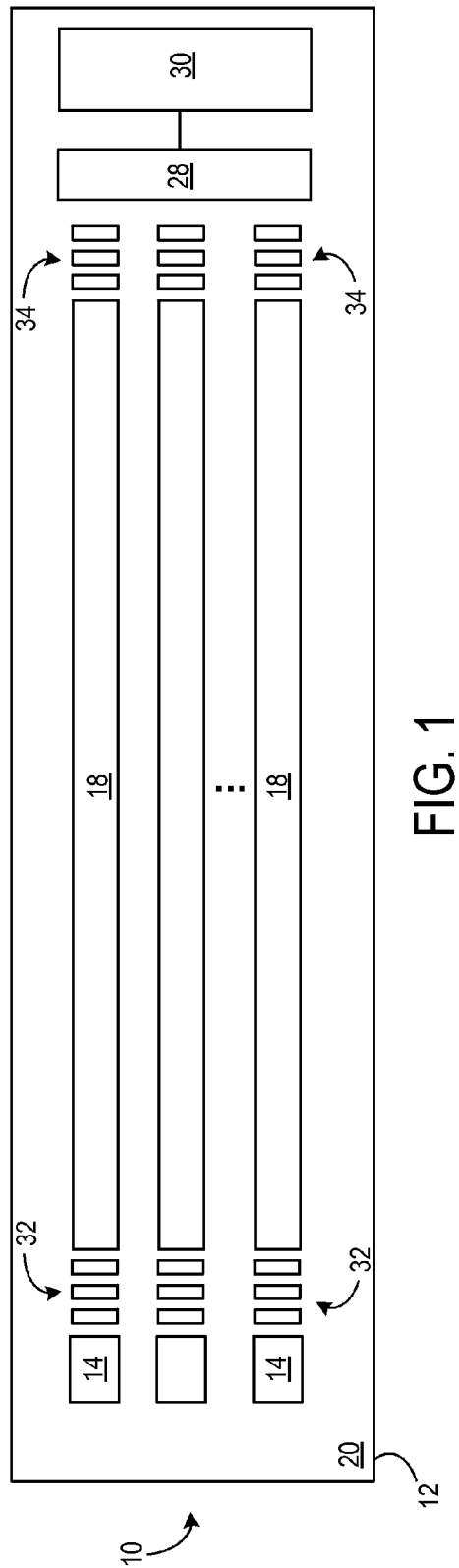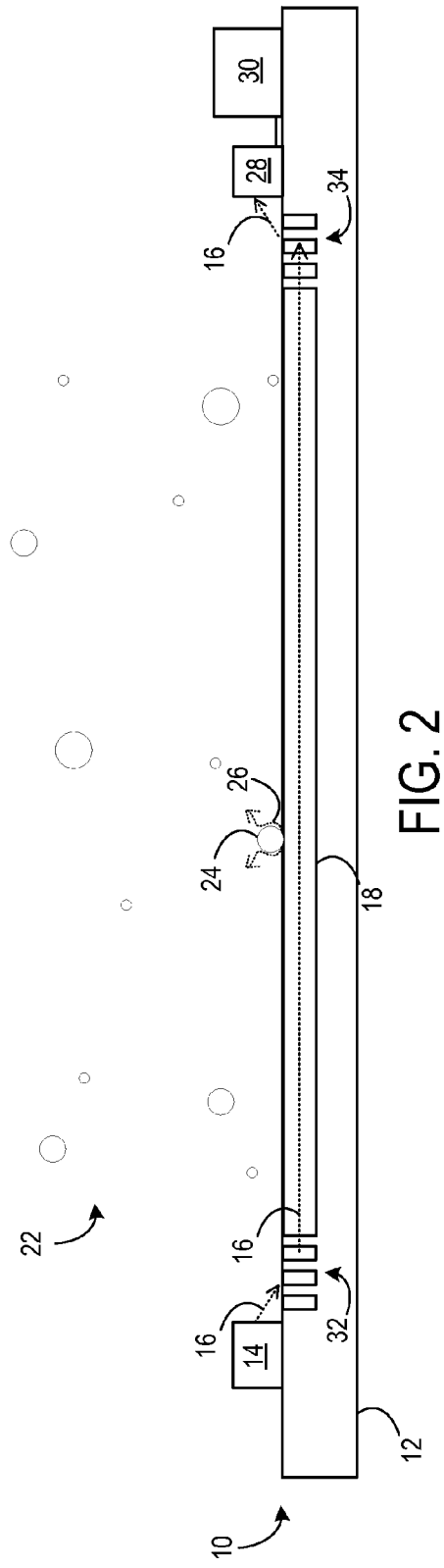

PARTICLE DETECTOR FOR PARTICULATE MATTER ACCUMULATED ON A SURFACE

BACKGROUND

Currently, determining air quality is not a simple endeavor. Particle counters such as light scattering particle counters and light blocking direct imaging particle counters may be used, but these devices have the drawback of not being sufficiently sensitive to detect extremely small particles at a competitive price point, and furthermore, such devices may include complex systems with moving parts that are prone to wear and tear over time. These drawbacks are barriers to the adoption of such sensors in an indoor environment such as a home or office environment where the effect of small particles on indoor air pollution is becoming a health concern.

The problem of air pollution is also a concern in outdoor settings, as it affects the performance of machines in the built environment such as solar panel arrays, heating ventilation and air conditioning (HVAC) systems, etc., and also because it affects how people live, work, and play outdoors. As one specific example, solar panels lose their effectiveness as particulate matter accumulates on their surfaces. However, since various other factors contribute to the effectiveness of a solar panel array, such as age of the solar panels, ambient operating temperature, shade and overcast skies, etc., it may be difficult to determine the extent to which a measured drop in effectiveness is affected by particulate build up on the front face of the solar panels. As a result, it is a challenge for the operator of the solar panel array to accurately determine when the solar panels should be cleaned to remove particulate build up. As a result, costly unneeded cleanings may occur, or the solar panels may not operate at optimum efficiency. The light scattering particle counters and light blocking direct imaging particle counters discussed above are not suitable for use in such large solar panel arrays due to their high cost relative to their sensitivity. Further, such sensors with moving parts may not be suitable for use in such an outdoor setting, where they may deteriorate more rapidly.

SUMMARY

Particle detectors and methods for detecting particulate matter accumulated on a surface are provided. According to one aspect, a particle detector is disclosed that comprises a substrate, an optical light source configured to emit light along a light path, a waveguide associated with the substrate, having a surface exposed to a gaseous environment and configured to accumulate on the surface particulate matter from the gaseous environment, a detector configured to receive the emitted light from the waveguide, and a controller configured to determine the intensity of the detected light and output an indication of an opacity of the surface of the waveguide with the accumulated particulate matter.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

FIG. 1 shows a top view of a particle detector according to a first embodiment.

FIG. 2 shows a side view of the particle detector of FIG. 1.

DETAILED DESCRIPTION

Figure 3:
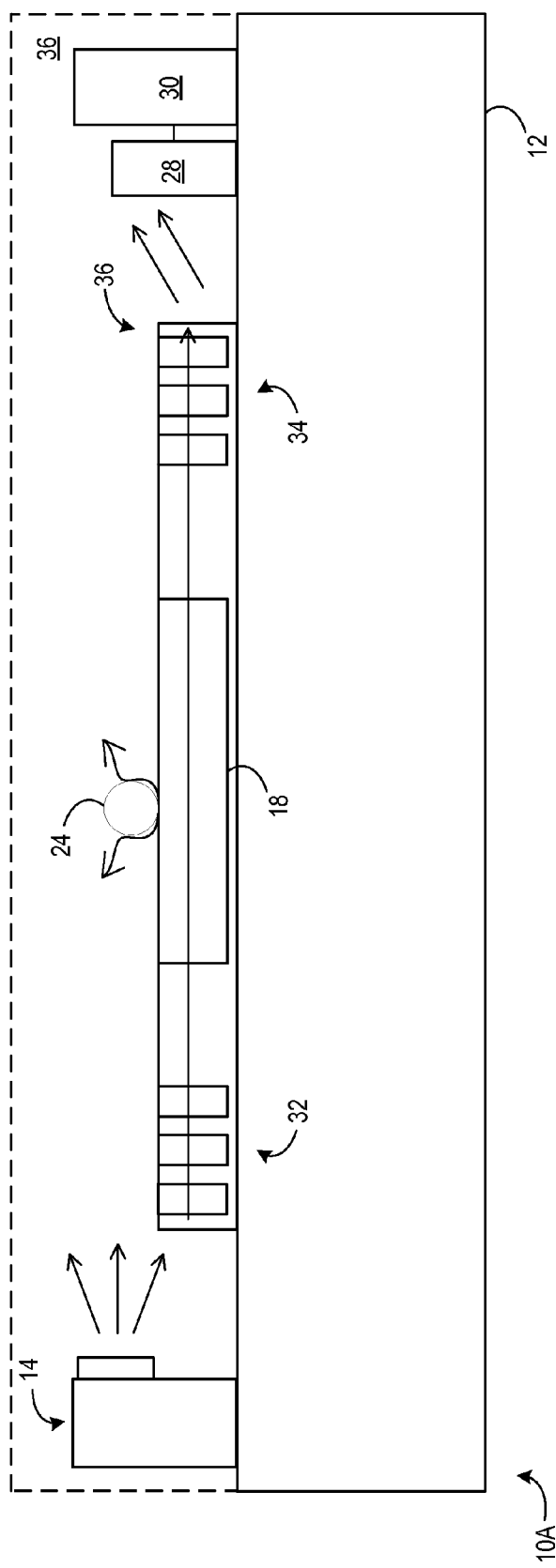
FIG. 3 shows a side view of the particle detector according to a second embodiment.

Particle detectors and methods for detecting particulate matter accumulated on a surface are described herein. FIG. 1 shows a top view of a particle detector 10 according to a first embodiment, and FIG. 2 shows a side view of the same. The particle detector 10 may comprise a substrate 12, an optical light source, depicted as an optical emitter 14, configured to emit light along a light path 16, and a waveguide 18 associated with the substrate 12. The waveguide 18 may be dielectric and have a surface 20 exposed to a gaseous environment 22 and configured to accumulate on the surface 20 particulate matter 24 from the gaseous environment 22. The waveguide 18 may be planar as shown, but it may also be any other reasonable shape. Due to the inclusion of the waveguide 18, light propagates through the waveguide 18 with low loss due to principles of total internal reflection. Not only does the light propagate through the waveguide 18, but it also induces an evanescent field which decays exponentially away from the surface 20. Particulate matter 24 that lands on the surface 20 interacts with the evanescent field, resulting in energy loss 26 and a reduction in light intensity for the light remaining in the waveguide 18. If the waveguide 18 and substrate 12 are configured to have a large form factor with respect to surface area, particulate matter 24 accumulating on the surface 20 can noticeably interact with the evanescent field even at low densities, thus providing the particle detector 10 with high sensitivity. Further, conventional particle counters may require increased air flow to be operable in a gaseous environment, but the increased surface area of the large form factor substrate 12 removes such a requirement. As an example, the substrate 12 with the large form factor may have a 22-inch diagonal measurement or larger. However, smaller form factor versions of the particle detector 10 may also be used with a trade-off in sensitivity due to the smaller sample size provided by the surface 20.

The particle detector 10 may comprise a detector 28 configured to receive the emitted light from the waveguide 18. The particle detector 10 may comprise a controller 30 configured to determine an intensity of the detected light. The controller 30 may compare the detected intensity with a known intensity at the light source to calculate the energy loss 26 and/or a correlated value. As the calculation is based on the intensity and not the wavelength, etc., the detector 28 and optical emitter 14 may be simpler and less costly than a highly specified version used in a conventional particle counter. The detector 28 may be, for example, a photoresistor or photodiode. The controller 30 may perform the calculation with use of a stored calibration table, for example. The controller 30 may be configured to control the optical emitter 14 and therefore have data indicated the known intensity at the light source, or else receive the data from a source controller within the light source. As the energy loss 26 directly correlates with the surface area of the surface 20 that is covered with particulate matter 24, therefore the change in intensity of light travelling through the waveguide 18 may be detected to track particulate accumulation. Further, the particle detector 10 may be configured to output an indication of an opacity of the surface 20 of the waveguide 18 with the accumulated particulate matter 24, discussed below in more detail with reference to FIG. 6.

The light source may include or be at least one optical emitter 14, which may be, for example, a laser diode or light-emitting diode. The particle detector 10 may include a first optical grating 32 disposed along the light path 16 configured to structure the light received from the optical emitter 14 into structured light and pass the structured light into the waveguide 18. Similarly, the particle detector 10 may further comprise a second optical grating 34 disposed along the light path 16 and configured to receive the structured light from the waveguide and pass the structured light to the detector 28. Although they may also consist of different materials, the substrate 12, the first optical grating 32, and the second optical grating 34 may instead consist of the same material. For example, the substrate 12 may be a glass panel, and the first optical grating 32, the second optical grating 34, and/or waveguide 18 may also be formed of glass. In this case, as the various glass components may be formed integrally from the same starting glass but at different refractive indices adjusted in the manufacturing process, specifically, the waveguide 18 may have a lower index than the substrate 12, the particle detector may be materially and visually a system composed of a single object. Such a particle detector 10 is structurally simple and the manufacture thereof is cost effective. The index of the glass can be adjusted locally at specified areas in the manufacturing process by methods including but not limited to chemical, physical, thermal, and optical treatments. In such a manner, the waveguide 18 and the optical gratings 32, 34 may be embedded in the substrate 12, as can be seen in FIG. 2. Thus, compared to existing particle counters such as light scattering particle counters and light blocking direct imaging particle counters, the particle detector 10 has a simple construction free of lenses and moving parts.

When the substrate 12 is a glass panel, the glass panel may be incorporated into a window, solar panel, display, or vehicle windshield, to provide merely a few examples. By detecting interaction between accumulated particulate matter 24 and the evanescent field of the waveguide 18, the particle detector 10 may operate without a functional film or other additional layer which may obstruct the view through the glass panel. Similar uses may exist for the substrate 12 when made of materials other than glass, such as various polymers. In this way, the particle detector 10 may be installed in a variety of products or devices that may function as they normally would without the particle detector 10, with the added benefit of opacity measurement of the surface of the product.

While a single, rectangular waveguide 18 may be used, multiple waveguides 18 may impart measurement accuracy and verification to the particle detector 10. Thus, the waveguide 18 may be one of a plurality of waveguides 18, the plurality of waveguides 18 formed in separate rows, as is shown in the first embodiment depicted in FIG. 1. The rows may be separated by the width of a single waveguide 18, although it is not particularly limited. In this case, each waveguide 18 may have an associated first optical grating 32 disposed along the respective light path configured to structure the light received from the optical emitter 14 into structured light and pass the structured light into the waveguide 18, and an associated second optical grating 34 disposed along the light path and configured to receive the structured light from the waveguide 18. Alternatively, some or all waveguides 18 may share optical gratings 32, 34 or even optical emitters 14. For simplicity, one optical emitter 14, one detector 28, and one controller 30 may be used; however, each of these may represent a system of similar components, as follows. For example, each waveguide 18 may have its own separate detector 28, and all of the detectors 28 are collectively shown as one detector 28. At least one detector 28 may be configured to receive the emitted light from each waveguide 18 via the respective second optical grating 34, and the controller 30 may be configured to determine the intensity of the detected light for each waveguide 18, and output an indication of an opacity of the surface 20 of at least one of the plurality of waveguides 18 with the accumulated particulate matter 24.

With multiple waveguides 18, the indication of opacity may be an average to represent the combined surface of the waveguides 18 and/or substrate 12. An accurate approximation of the opacity of the entire surface of the substrate 12 may be given when a sufficient amount of the surface of the substrate 12 is covered by the waveguides 18 and a sufficient number of detected intensities are compared. The average may be calculated in several ways, including as a mean, median, or mode of the opacities of some or all of the waveguides 18. The opacity of various waveguides 18 may be weighted differently than others depending on geometric position, size, presumed accuracy, etc. Further, the multiple sample pools provided by the multiple waveguides may give the opportunity to verify results. For example, if the particle detector is used outside, one waveguide 18 could be covered with a mud splatter, and the lowered intensity could inflate the opacity of the surface 20 that is assumed to be caused by accumulated particulate matter. However, if at least another waveguide 18 does not have the same splatter, a more accurate calculation can be made by disregarding the intensity from the dirty waveguide 18 as an outlier. Thus, the controller 30 may be configured to compare the intensity of the detected light for at least two waveguides 18, and if a difference between the at least two intensities exceeds a predetermined threshold, the controller may be configured to output an error message, discussed below with reference to FIG. 6. Further, a user may be notified that the particle detector 10 is in need of cleaning or calibration.

The waveguides 18 are not limited to the embedded configuration discussed above. FIG. 3 shows a side view of a particle detector 10A according to a second embodiment. It will be appreciated that like components present in various embodiments are referenced with the same reference characters and descriptions thereof will not be repeated for the sake of brevity. In the second embodiment, at least the waveguide 18 may be formed in a film 36 adhered to the substrate 12. Along with the waveguide 18, the optical gratings 32, 34 may also be formed in the film 36 if included. The optical emitter 14, detector 28, and controller 30 may be formed in the film 36 (shown in dotted lines in FIG. 3) if unobtrusive, although they may also be installed separately (shown in solid lines in FIG. 3). In contrast to the embedded embodiments discussed above, this embodiment may allow for easy retrofitting of legacy devices by applying the film 36 to the substrate 12 already incorporated in such a device. Further, such a film 36 may be used on an opaque substrate 12 such as a countertop, wall, etc., widening the potential applications of the particle detector 10A. For instance, a chef in a professional kitchen may use the particle detector 10A to monitor the cleanliness of a portion of the countertop and ensure that proper cleaning is performed.

Figure 4:
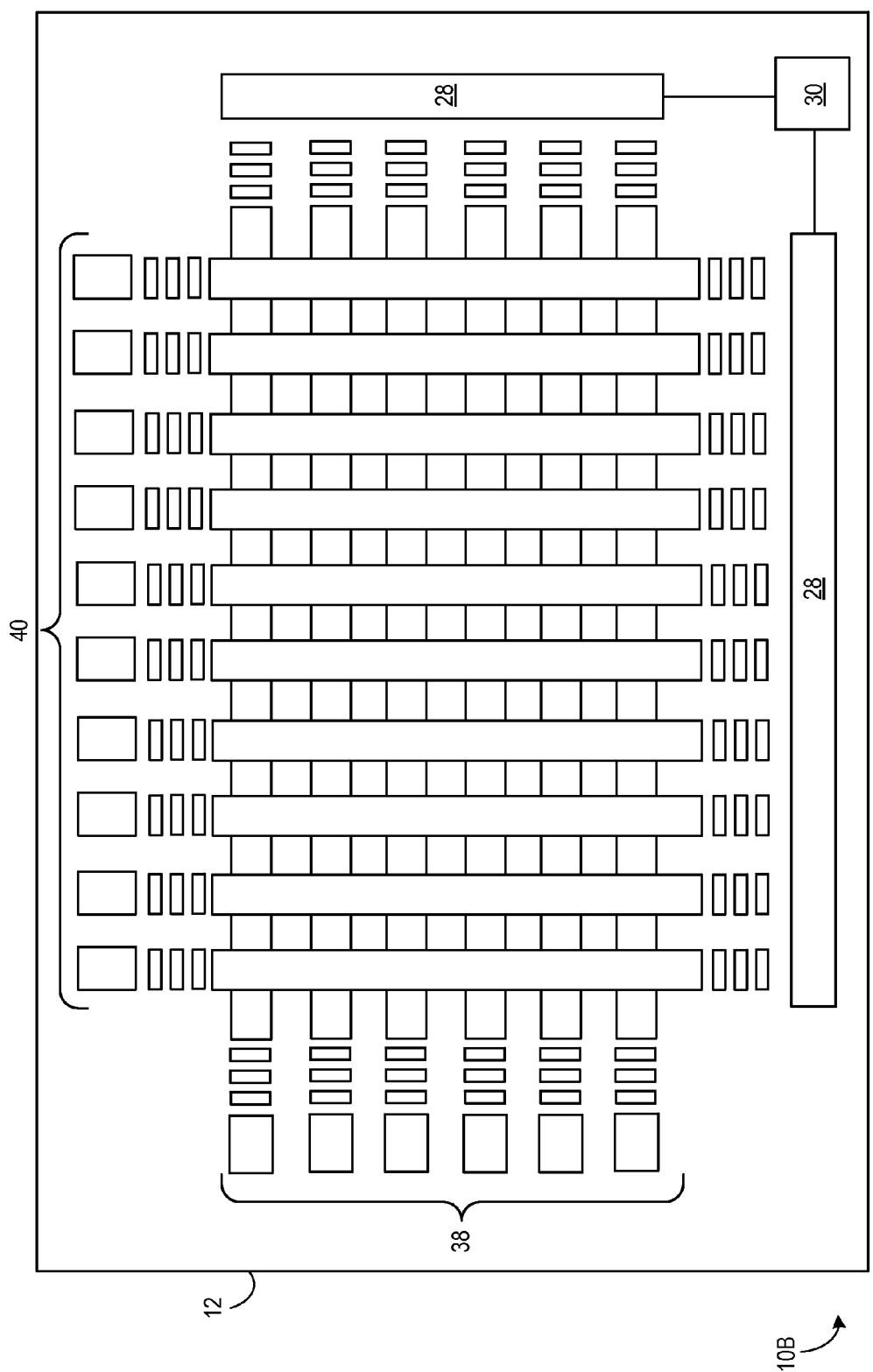
FIG. 4 shows a top view of the particle detector according to a third embodiment.

The waveguide 18 is not limited to the row configuration shown in FIG. 1. Alternatively, FIG. 4 shows a top view of a particle detector 10B according to a third embodiment. According to the third embodiment, the waveguide 18 may be one of a plurality of waveguides 18, the plurality of waveguides 18 being formed in a matrix pattern. As shown in FIG. 4, the waveguides 18 may be disposed in two sets, e.g., rows 38 and columns 40, with one set disposed on top of the other, thus forming a matrix or grid pattern. The two sets 38, 40 may be perpendicular but they may also be skewed. Detecting the intensity of light travelling through each waveguide 18 allows for the potential of pinpointing the location of particulate matter 24 with coordinates from waveguide 18 row and column numbers where the particulate matter 24 is detected. For a very large substrate 12 such as a solar panel or solar panel array, the particle detector 10B may enable cleaning operations to be targeted only to areas in true need of cleaning, and spare areas that are not truly in need of cleaning, where cleaning would result in wasted resources. For example, areas determined to be at a detected opacity that is below a threshold may not be in need of cleaning, while areas determined to be at a detected opacity that is above the threshold may be in need of cleaning.

Figure 5:
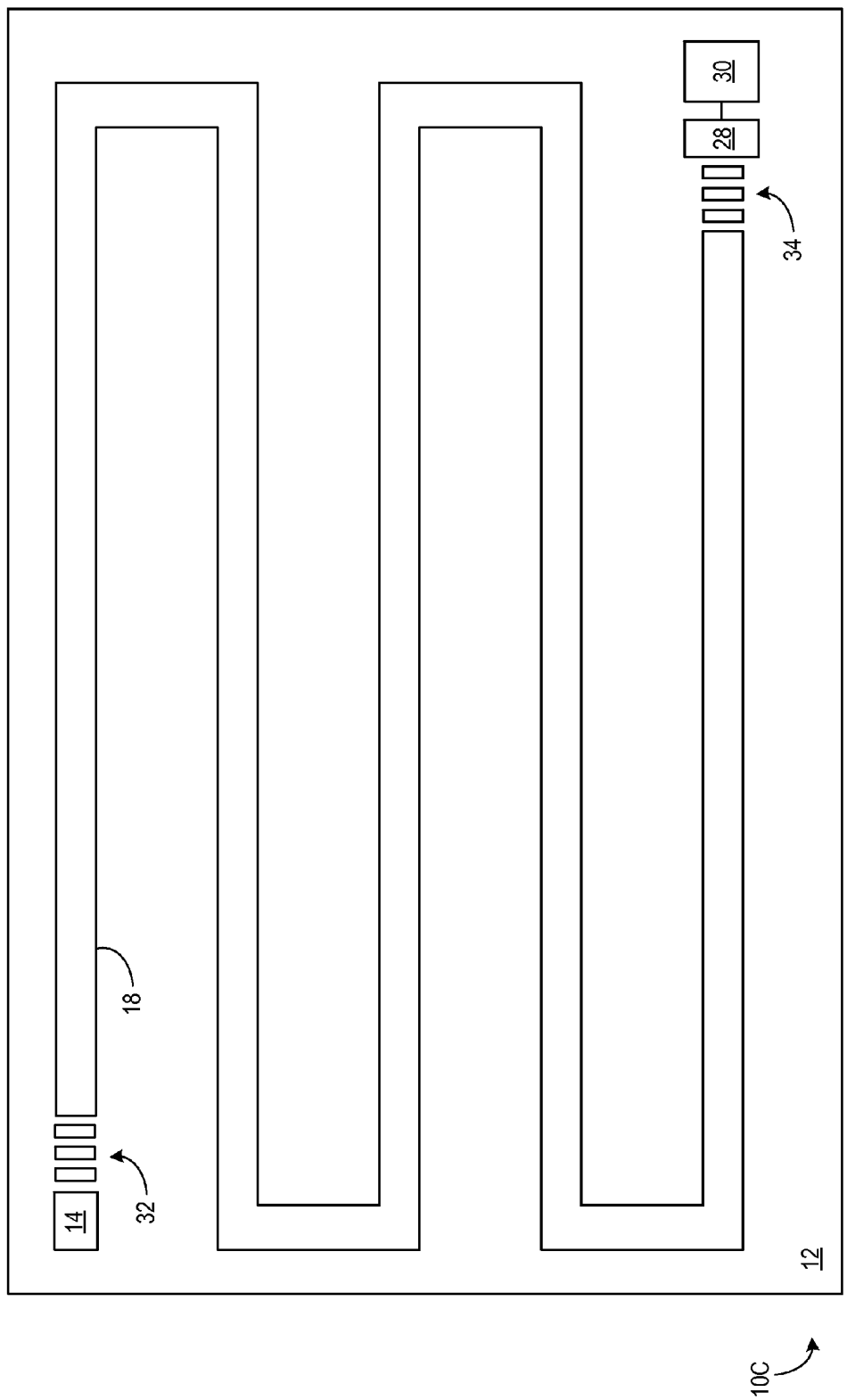
FIG. 5 shows a top view of the particle detector according to a fourth embodiment.

FIG. 5 shows a top view of a particle detector 10C according to a fourth embodiment. According to the fourth embodiment, the waveguide 18 may be formed in a serpentine or hairpin pattern. As shown in FIG. 5, the waveguide 18 extends away from the light emitter 14 then doubles back in the opposite direction. The number of loops or bends is not particularly limited and may be as few as one, for example. The serpentine pattern allows the waveguide 18 to cover a greater percentage of surface area while only using a single light emitter 14 and detector 28. By covering a greater percentage of the surface area with the waveguide 18, the sample area is increased and the ability of the sample to more accurately represent the degree of particulate matter 24 accumulated on the entire surface is improved.

Figure 6:
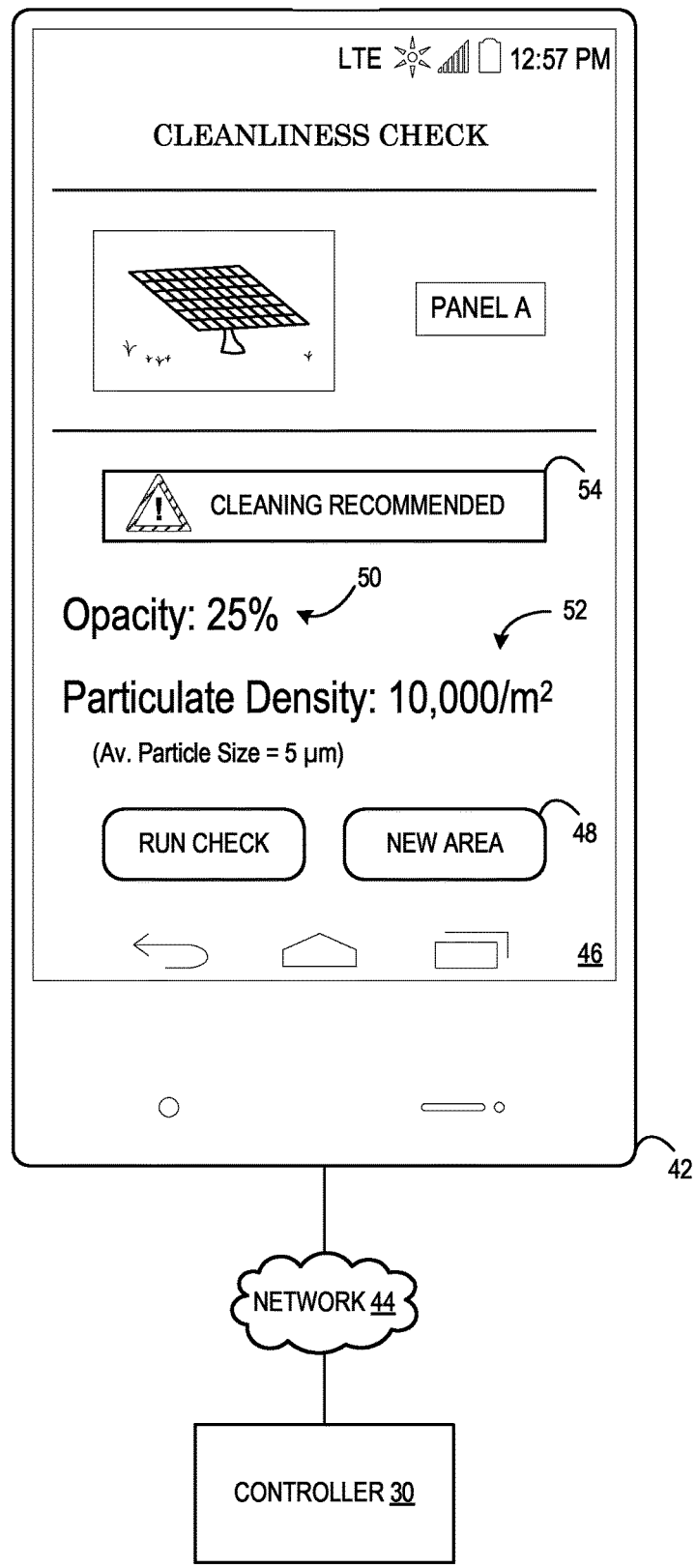
FIG. 6 shows a displayed output from the particle detector.

FIG. 6 shows a displayed output from the particle detector 10. Any combination of the above-described embodiments may be suitable to produce the output of FIG. 6. The controller 30 of the particle detector 10 may be configured to connect to a computing device 42, depicted here as a smartphone, via a network 44. The controller 30 may be wirelessly or physically connected to the computing device 42, or even integrated therein. For example, if the substrate 12 is incorporated into a display device, then the display device itself may display the output from the particle detector 10, which is received wirelessly or through a wired connection. However, a wireless connection via network 44 may allow for mobile notifications of the status of the particle detector 10, remote control, and multi-user access.

Computing device 42 may include a display 46. In the depicted example, the computing device 42 may be configured to execute an application program named "CLEANLINESS CHECK" to monitor the opacity of the waveguides 18 and/or substrate 12. The application program may display a graphical user interface (GUI) navigable by a user. In FIG. 6, the user has selected the solar panel "PANEL A" in which the particle detector 10 is installed. The user may be able to use the same application program to track multiple panels or other devices each with a particle detector 10 installed. For instance, the NEW AREA button 48 may allow the user to choose another monitored surface other than PANEL A.

As mentioned above, the particle detector 10 may be configured to output an indication 50 of the opacity of the surface 20 of the waveguide 18 with the accumulated particulate matter 24. Here, the indication 50 of the opacity (25%) is output visually on the GUI on the display 46. However, the indication 50 may instead be output in any suitable manner, including as a text message, an email, a pop-up GUI element, overlaid text, an audio message, etc. The controller 30 may be further configured to output an indication 52 of a density of the accumulated particulate matter 24 based on the opacity. In the example of FIG. 6, the density is indicated to be $10,000/m^2$. As with the indication 50 of the opacity, the indication 52 of the density may be output in any suitable manner. The controller 30 may output the density expressed in terms of average particle size based on the opacity, shown here as 5 µm.

The controller 30 may be configured to output an alert message 54 based on the opacity, the alert message 54 being a service alert message or pollution alert message. The alert message 54 may be sent if the opacity exceeds a predetermined threshold, which may be set by the user or manufacturer. In this manner, the user may be notified that the device in which the particle detector 10 is installed is in need of cleaning, or that current pollution conditions are unsafe. The alert message 54 may also be the error message resulting from the difference in intensity between two waveguides 18 exceeding the threshold, indicating a dirty or malfunctioning particle detector 10.

Figure 7:
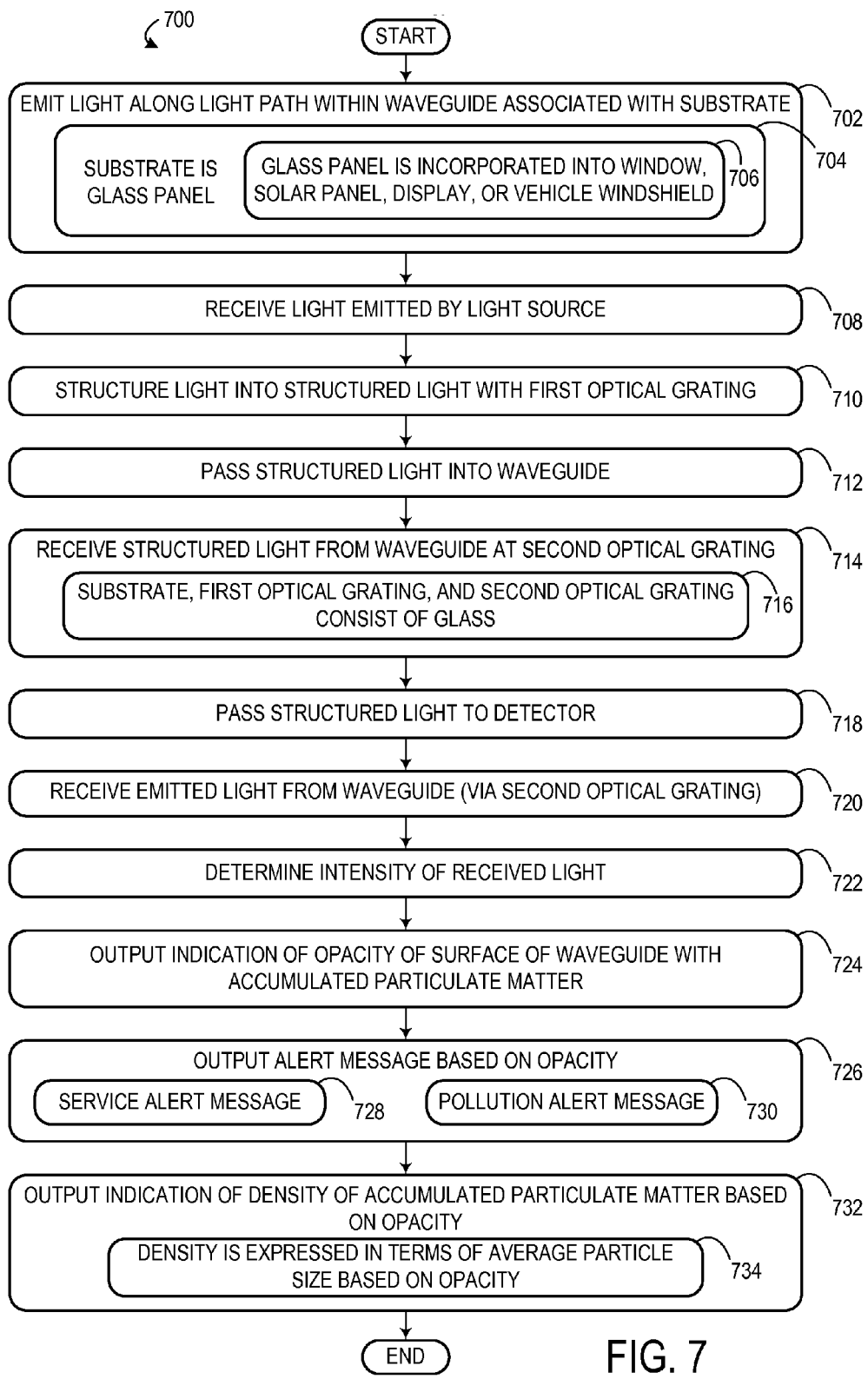
FIG. 7 shows a flowchart of a method for detecting particulate matter accumulated on a surface.

FIG. 7 shows a flowchart of a method 700 for detecting particulate matter accumulated on a surface. The following description of method 700 is provided with reference to the components of the particle detectors 10, 10A, 10B, or 10C or any combination thereof described above and shown in FIGS. 1-6. It will be appreciated that method 700 may also be performed in other contexts using other suitable components.

With reference to FIG. 7, at 702 the method 700 may include emitting light along a light path within a waveguide associated with a substrate. At 704 the substrate may be a glass panel, and at 706 the glass panel may be incorporated into a window, solar panel, display, or vehicle windshield. At 708 the method 700 may include receiving the light emitted by a light source. At 710 the method 700 may include structuring the light into structured light with a first optical grating, and at 712 the method 700 may include passing the structured light into the waveguide.

At 714 the method 700 may include receiving the structured light from the waveguide at a second optical grating, and at 716 the substrate, the first optical grating, and the second optical grating may consist of glass. At 718 the method 700 may include passing the structured light to the detector. At 720 the method 700 may include receiving the emitted light from the waveguide, which may be via the second optical grating if included.

At 722 the method 700 may include determining an intensity of the received light. At 724 the method 700 may include outputting an indication of an opacity of the surface of the waveguide with the accumulated particulate matter. At 726 the method 700 may include outputting an alert message based on the opacity. At 728 the alert message may be a service alert message, and at 730 the alert message may be a pollution alert message. At 732 the method 700 may include outputting an indication of a density of the accumulated particulate matter based on the opacity, and at 734 the density may be expressed in terms of average particle size based on the opacity.

In some embodiments, the above systems and methods may take advantage of large form factor glass panels to include large surface area embedded waveguide(s) that allow light to propagate with minimal loss. Whether large or small, the waveguides may accumulate particulate matter that interacts with an evanescent field at the surface of the waveguides in a manner that may be monitored by a drop in intensity of light travelling through the waveguides. A particle detector as described above may be simpler, more economical, and more sensitive to small particles as compared to conventional particle counters, and may also have fewer moving parts, increasing the sturdiness and lifespan of the detector.

In some embodiments, the methods and processes described herein may be tied to a computing system of one or more computing devices. In particular, such methods and processes may be implemented as a computer-application program or service, an application-programming interface (API), a library, and/or other computer-program product.

Figure 8:
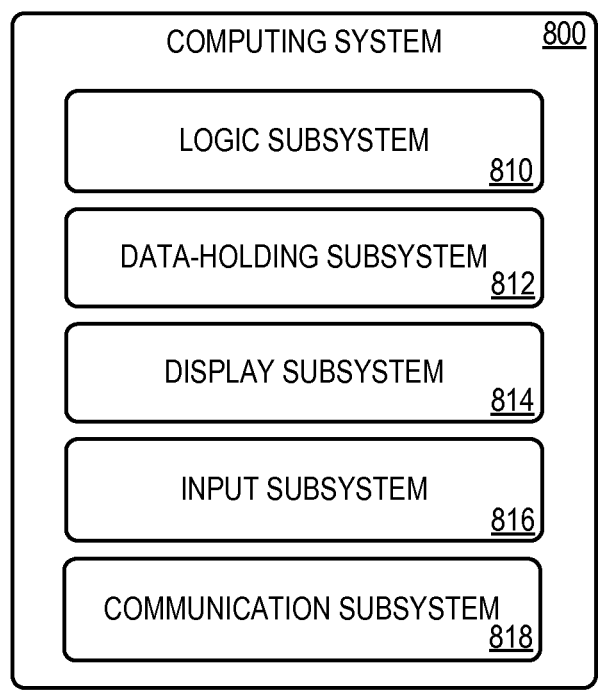
FIG. 8 shows a simplified schematic diagram of a computing system.

FIG. 8 shows a simplified schematic diagram of a non-limiting embodiment of a computing system 800 that can enact one or more of the methods and processes described above. Computing system 800 is shown in simplified form. Computing system 800 may take the form of one or more controllers, personal computers, server computers, tablet computers, home-entertainment computers, network computing devices, mobile computing devices, mobile communication devices (e.g., smartphone), and/or other computing devices. The controller 30 and computing device 42 of FIG. 6 may be one example of computing system 800.

Computing system 800 includes a logic subsystem 810 and a data-holding subsystem 812. Computing system 800 may optionally include a display subsystem 814, input subsystem 816, communication subsystem 818, and/or other components not shown in FIG. 7.

Logic subsystem 810 includes one or more physical devices configured to execute instructions. For example, the logic subsystem may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic subsystem may include one or more processors configured to execute software instructions. Additionally or alternatively, the logic subsystem may include one or more hardware or firmware logic subsystems configured to execute hardware or firmware instructions. Processors of the logic subsystem may be single-core or multi-core, and the instructions executed thereon may be configured for sequential, parallel, and/or distributed processing. Individual components of the logic subsystem optionally may be distributed among two or more separate devices, which may be remotely located and/or configured for coordinated processing. Aspects of the logic subsystem may be virtualized and executed by remotely accessible, networked computing devices configured in a cloud-computing configuration.

Data-holding subsystem 812 includes one or more physical devices configured to hold instructions executable by the logic subsystem to implement the methods and processes described herein. When such methods and processes are implemented, the state of data-holding subsystem 812 may be transformed e.g., to hold different data.

Data-holding subsystem 812 may include removable and/or built-in devices. Data-holding subsystem 812 may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Data-holding subsystem 812 may include volatile, nonvolatile, dynamic, static, read/write, read-only, random-access, sequential-access, location-addressable, file-addressable, and/or content-addressable devices.

It will be appreciated that data-holding subsystem 812 includes one or more physical devices. However, aspects of the instructions described herein alternatively may be propagated by a communication medium (e.g., an electromagnetic signal, an optical signal, etc.) that is not held by a physical device for a finite duration.

Aspects of logic subsystem 810 and data-holding subsystem 812 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The term "application program" may be used to describe an aspect of computing system 800 implemented to perform a particular function. In some cases, an application program may be instantiated via logic subsystem 810 executing instructions held by data-holding subsystem 812. It will be understood that different application programs may be instantiated from the same application, service, code block, object, library, routine, API, function, etc. Likewise, the same application program may be instantiated by different applications, services, code blocks, objects, routines, APIs, functions, etc. The term "application program" may encompass individual or groups of executable files, data files, libraries, drivers, scripts, database records, etc.

When included, display subsystem 814 may be used to present a visual representation of data held by data-holding subsystem 812. This visual representation may take the form of a GUI. As the herein described methods and processes change the data held by the data-holding subsystem, and thus transform the state of the data-holding subsystem, the state of display subsystem 814 may likewise be transformed to visually represent changes in the underlying data. Display subsystem 814 may include one or more display devices utilizing virtually any type of technology. Such display devices may be combined with logic subsystem 810 and/or data-holding subsystem 812 in a shared enclosure, or such display devices may be peripheral display devices.

When included, input subsystem 816 may comprise or interface with one or more user-input devices such as a keyboard, mouse, or touch screen.

When included, communication subsystem 818 may be configured to communicatively couple computing system 800 with one or more other computing devices. Communication subsystem 818 may include wired and/or wireless communication devices compatible with one or more different communication protocols. As non-limiting examples, the communication subsystem may be configured for communication via a wireless telephone network, or a wired or wireless local- or wide-area network, such as the network 44 of FIG. 6. In some embodiments, the communication subsystem may allow computing system 800 to send and/or receive messages to and/or from other devices via a network such as the Internet.

It will be understood that the configurations and/or approaches described herein are exemplary in nature, and that these specific embodiments or examples are not to be considered in a limiting sense, because numerous variations are possible. The specific routines or methods described herein may represent one or more of any number of operating strategies. As such, various acts illustrated and/or described may be performed in the sequence illustrated and/or described, in other sequences, in parallel, or omitted. Likewise, the order of the above-described method steps may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A particulate matter detector comprising:
   a substrate;
   an optical light source configured to emit light having an intensity along a light path;
   a waveguide associated with the substrate, having a surface exposed to a gaseous environment and the waveguide surface configured to accumulate directly thereon particulate matter from the gaseous environment;
   a detector configured to receive the emitted light from the waveguide; and
   a controller configured to determine a change in the intensity of the light emitted from the waveguide, and output an indication of an opacity of the surface of the waveguide with the accumulated particulate matter thereon based on a change in intensity of the emitted light; wherein the controller determines an indication of an opacity of the surface of the waveguide with the accumulated particulate matter by comparing the detected intensity with a known intensity at the optical light source.

2. The particulate matter detector of claim 1, wherein the light source includes an optical emitter; and
   the particulate matter detector includes a first optical grating disposed along the light path and configured to structure the light received from the optical emitter into structured light and pass the structured light into the waveguide.

3. The particulate matter detector of claim 2, further comprising:
   a second optical grating disposed along the light path and configured to receive the structured light and pass the structured light to the detector.

4. The particulate matter detector of claim 1, wherein the controller is further configured to output an indication of a density of the accumulated particulate matter based on the opacity.

5. The particulate matter detector of claim 4, wherein the controller outputs the density expressed in terms of average particle size based on the opacity.

6. The particulate matter detector of claim 1, wherein the substrate, the first optical grating, and the second optical grating consist of a same material.

7. The particulate matter detector of claim 1, wherein the substrate is a glass panel.

8. The particulate matter detector of claim 7, wherein the glass panel is incorporated into a window, solar panel, display, or vehicle windshield.

9. The particulate matter detector of claim 1, wherein the controller is configured to output an alert message based on the opacity, the alert message being a service alert message or pollution alert message.

10. The particulate matter detector of claim 1, wherein at least the waveguide is formed in a film adhered to the substrate.

11. The particulate matter detector of claim 1, wherein:
    the waveguide is formed in a serpentine pattern; or
    the waveguide is one of a plurality of waveguides, the plurality of waveguides formed in a matrix pattern.

12. The particulate matter detector of claim 1, wherein the waveguide is one of a plurality of waveguides, the plurality of waveguides formed in separate rows.

13. A method for detecting particulate matter accumulated on a surface of a waveguide, the method comprising:
    accumulating the particulate matter from a gaseous environment directly on the surface of a waveguide;
    emitting light having an intensity along a light path within the waveguide associated with a substrate;
    receiving the emitted light from emitted from the waveguide;
    determining the intensity of the received light;
    outputting an indication of an opacity of the waveguide surface based on a change in the intensity of the emitted light resulting from the particulate matter; wherein the indication of an opacity of the surface of the waveguide with the accumulated particulate matter is calculated by comparing the intensity of the received light with the intensity of the emitted light.

14. The method of claim 13, further comprising:
    receiving the light emitted by a light source;
    structuring the light into structured light with a first optical grating; and
    passing the structured light into the waveguide.

15. The method of claim 14, further comprising:
    receiving the structured light from the waveguide at a second optical grating; and
    passing the structured light to the detector.

16. The method of claim 14, further comprising outputting an indication of a density of the accumulated particulate matter based on the opacity, wherein the density is expressed in terms of average particle size based on the opacity.

17. The method of claim 13, wherein the substrate, the first optical grating, and the second optical grating consist of glass, and the substrate is a glass panel.

18. The method of claim 17, wherein the glass panel is incorporated into a window, solar panel, display, or vehicle windshield.

19. The method of claim 13, further comprising outputting an alert message based on the opacity, the alert message being a service alert message or pollution alert message.

20. A particle detector incorporated into a solar panel, the particle detector comprising:
    a substrate;
    an optical light source including at least one optical emitter configured to emit light along a respective light path;
    a plurality of waveguides formed in separate rows, each waveguide having a surface exposed to a gaseous environment and configured to accumulate on the surface particulate matter from the gaseous environment, an associated first optical grating disposed along the respective light path configured to structure the light received from the optical emitter into structured light and pass the structured light into the waveguide, and an associated second optical grating disposed along the light path and configured to receive the structured light from the waveguide;

at least one detector configured to receive the emitted light from each waveguide via the respective second optical grating; and a controller configured to determine an intensity of the detected light for each waveguide, and output an indication of an opacity of the surface of at least one of the plurality of waveguides with the accumulated particulate matter; wherein the controller is configured to compare the intensity of the detected light for at least two waveguides, and if a difference between the at least two intensities exceeds a predetermined threshold, the controller is configured to output an error message.

* * * * *